United States Patent [19]

Seprödi et al.

[11] Patent Number: 4,600,705
[45] Date of Patent: Jul. 15, 1986

[54] GONADOLIBERIN DERIVATIVES CONTAINING A β-ASPARTYL GROUP, A PROCESS FOR THE PREPARATION THEREOF AND PHARMACEUTICAL PREPARATIONS CONTAINING THEM

[75] Inventors: Janos Seprödi; István Teplán; Imre Mezö; Judit Érchegyi, all of Budapest, Hungary

[73] Assignee: Richter Gedeon Veyteszeti Gyar R.T., Hungary

[21] Appl. No.: 594,880

[22] Filed: Mar. 29, 1984

[30] Foreign Application Priority Data

Mar. 29, 1983 [HU] Hungary ............................ 1062/83

[51] Int. Cl.$^4$ ...................... A61K 37/02; C07C 103/52
[52] U.S. Cl. .................. 514/15; 260/112.5 R; 260/112.5 LH
[58] Field of Search .................. 260/112.5 LH; 514/15

[56] References Cited

U.S. PATENT DOCUMENTS 4,118,483 10/1978 König et al. ............. 260/112.5 LH
4,395,400 7/1983 König et al. ............. 260/112.5 LH

OTHER PUBLICATIONS

*Chemical Abstracts,* vol. 100, 1984, Abst. No. 156992u.
*Chemical Abstracts,* vol. 101, 1984, Abst. No. 204336c.

Primary Examiner—Delbert R. Phillips
Assistant Examiner—F. T. Moezie
Attorney, Agent, or Firm—Keil & Weinkauf

[57] ABSTRACT

The invention relates to novel gonadoliberine derivatives of the general formula (I)

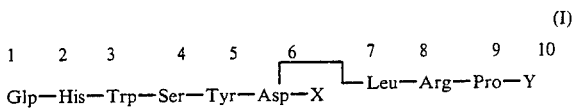

(I)

wherein
X represents an —O—R group wherein R is a benzyl group or a $C_{1-4}$ alkyl group, an

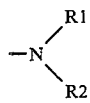

group wherein R1 and R2 independently stand for hydrogen, a $C_{1-5}$ alkyl, aryl, aryl-$C_{1-2}$-alkyl, morpholino, 1-indolinyl or 1-pyrrolidinyl group,
Y is a glycine amide or a $C_{1-4}$-alkyl-amide group,
the addition salts thereof formed with acids used in therapy and complexes thereof as well as pharmaceutical compositions containing them, furthermore to a process for the preparation of the above compounds.

The reproductive processes of vertebrates can be advantageously influenced with the compounds of general formula (I).

3 Claims, No Drawings

GONADOLIBERIN DERIVATIVES CONTAINING A β-ASPARTYL GROUP, A PROCESS FOR THE PREPARATION THEREOF AND PHARMACEUTICAL PREPARATIONS CONTAINING THEM

The invention relates to novel gonadoliberine derivatives of the general formula (I),

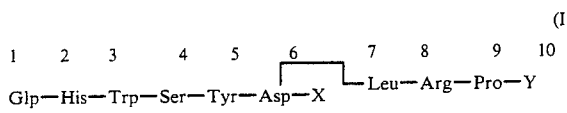

the addition salts formed with therapeutically usable acids and complexes thereof as well as to pharmaceutical compositions containing them. In the general formula (I)

X represents an —O—R group wherein R is a benzyl group or a $C_{1-4}$ alkyl group, an

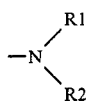

group wherein R1 and R2 independently stand for hydrogen, a $C_{1-5}$ alkyl, aryl or aryl $C_{1-2}$-alkyl group, or they stand together with the adjacent nitrogen atom for a morpholino, 1-indolinyl or 1-pyrrolidinyl group, Y is a glycine amide or a $C_{1-4}$-alkyl-amide group.

The abbreviations used in the formula are identical with the nomenclature accepted in peptide chemistry which is disclosed e.g. in J. Biol. Chem. [241, 527 (1966); 247, 977 (1972)]. Other abbreviations used in this specification are as follows: EA=ethylamino; DEA=diethylamino; CBA=cyclobutylamino; FBA=(1,1-dimethyl-2-phenyl)-ethylamino; IND=1-indolinyl; PIR=1-pyrrolidinyl, ANI=phenylamino; BOC=tert.-butyloxy-carbonyl group.

It is a general property of the gonadoliberine (other names known in literature: gonadotrop releasing hormone, GnRH, LH-RH, luteinizing and folliculus stimulating hormone, LH/FSH-RH) and its known derivatives that they are able of releasing the luteinizing hormone (LH) and the folliculus stimulating hormone (FSH).

From literature it is known (M. Monahan et al., Biochemistry 12, 4616–4620 /1973/; J. Sandow et al., Control of Ovulation, Butterworths, London, 1978, pp. 49-70) that those derivatives of gonadoliberine which contain in position 6, instead of a glycine moiety, amino acids of configuration D or the derivatives thereof, furthermore those wherein the glycine amide moiety in position 10 is substituted by amide groups with aliphatic carbon chain (M. Fujino et al., J. Med. Chem. 16, 1144 (1973)), exert a biological effect which is increased and longer in relation to that of gonadoliberine. In contradiction to this it is known, too, that the gonadoliberine derivatives containing an amino acid of L-configuration in position 6, such as L-alanine, L-proline, L-valine (Monahan et al., Biochemistry 12, 4616 /1973/). L-isoleucine (D. Coy et al., J. Med. Chem. 16, 1140 /1973/) or amino acids having no asymmetry centre, such as gamma-amino butyric acid, β-alanine (J. Rivier et al., Peptides: Chemistry, Structure, Biology, Ed. R. Walter, J. Meienhofer, Ann Arbor Science Publishers Inc., Michigan, p. 803 /1975/) or sarcosine (W. Arnold et al., J. Med. Chem. 17, 314 /1974/) possess only a minimum activity.

Concerning the LH-release only one special gamma-lactame ring of L-configuration proved to be a biologically efficacious substituent in position 6 (Veber et al., Science 210, 656 /1980/).

The invention aims at providing novel gonadoliberine derivatives which exert a more advantageous effect than the known analogues.

The invention is based on the recognition that if L-aspartic acid is built through its β-carboxyl group into position 6 of the peptide chain of gonadoliberine and at the same time its alpha-carboxyl group is left free or attached to a relatively small atom group, the thus-obtained gonadoliberine derivatives exert a biological effect similar to or even better than that of the gonadoliberine derivatives containing a D-amino acid in position 6.

The compounds of general formula (I) can be prepared as follows:

($a_1$) a tetra- or pentapeptide of the general formula (II)

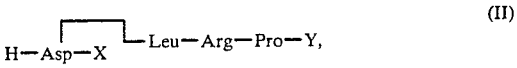

wherein X and Y are as defined above, is condensed with the pentapeptide azide of the formula Glp-His-Trp-Ser-Tyr-$N_3$ or ($a_2$) a hexapeptide of the general formula (III),

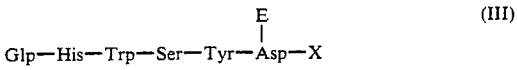

wherein X is as defined above and E is a hydroxyl, azide or N-succinimide-oxy group or a phenoxy group optionally substituted with a nitro group or one or more halogen atoms, preferably a p-nitro, 2,4,6-trichlorophenoxy, pentachlorophenoxy or pentafluorophenoxy group, is condensed with a tri- or tetrapeptide of the general formula (IV),

wherein Y is as defined above, or ($a_3$) when compounds of the general formula (I) are to be prepared wherein a glycine amide group is at the C-terminal of the molecule, to a chloromethylated polystyrene-divinyl-benzene resin containing 1-3%, preferably 2%, of cross-links, BOC-glycine is coupled, from the thus-obtained compounds of formula (V)

the BOC group is split off, then starting from the C-terminal amino acids having protective groups are coupled in an appropriate sequence to the peptide polymer by periodical repetition of the splitting and coupling operations, and the ready peptide is split off from the peptide polymer by ammonolysis and the protective groups are eliminated by a treatment with hydrogen fluoride, or ($a_4$) when compounds of general formula (I) are to be prepared wherein a glycine amide group is at the C-terminal of the molecule, BOC-glycine is coupled to a polystyrene-divinyl-benzene resin containing benzhydryl-amino groups and 1-3%, preferably 2% of cross links, and from the thus-obtained compound of formula (VI)

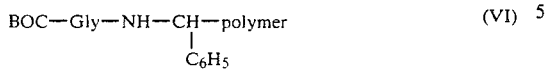

the BOC group is split off, then starting from the C-terminal amino acids provided with protective groups are coupled in an appropriate sequence to the peptide polymer by periodically repeating the splitting and coupling operations and the ready peptide is split off and the protective groups are eliminated from the peptide polymer by treatment with hydrogen fluoride, or (a5) when compounds of general formula (I) are to be prepared wherein a -Pro-Y group is at the C-terminal of the molecule, wherein Y is as defined above, BOC-proline is attached to a chloro-methylated polystyrenedivinyl-benzene resin containing 1-3%, preferably 2% of cross-links, and from the thus-obtained compound of formula (VII)

BOC-Pro-O-CH$_2$-polymer    (VII)

the BOC group is split off, then starting from the C-terminal the amino acids provided with protective groups are coupled in an appropriate sequence to the peptide polymer by periodically repeating the splitting and coupling operations, and the ready peptide is split off from the peptide polymer by aminolysis and the protective groups are eliminated by treatment with hydrogen fluoride.

In process (a$_1$) a tetra- or pentapeptide component can be prepared by fragment condensation or stepwise chain elongation in a manner known per se by activation with an azide, mixed anhydre, carbodiimide, active ester or an other activating group. Suitably the H-Leu-Arg(NO$_2$)-Pro-Y tri- or tetrapeptide—wherein Y is as defined above—is acylated with the aspartic acid derivatives of general formula (VIII)

wherein Z is a tert.-butyloxy-carbonyl or a benzyloxycarbonyl group, and X and E are as defined above—having a tert.-butyloxycarbonyl or benzyloxycarbonyl protective group at their amino group, whereafter the protective groups are eliminated from the obtained compound.

In process (a$_2$) the hexapeptide of formula (III) is suitably prepared by acylating the aspartic acid derivative of formula (IX)

wherein X is as defined above, R$_3$ represents hydrogen, a methyl, benzyl or tert.-butyl group—with a Glp-His-Trp-Ser-Tyr-N$_3$ pentapeptide azide.

The solid-phase peptide synthesis methods used in process (a$_3$) are known in literature (J. M. Stewart: "Solid Phase Peptide Synthesis", Freeman and Co., San Francisco, 1969).

Numerous gonadoliberine analogues were prepared by automatically controlled solid-phase synthesis (D. Coy et al., Biochemistry 13, 323 /1974/; D. Coy et al., J. Med. Chem. 19, 423 /1976/); the process a$_4$) differs from the known ones in using an amino acid derivative of general formula (X),

wherein X is as defined above, R$_3$ is hydrogen, a p-nitrophenyl group or a pentafluoro-phenyl group, as amino acid in position 6. For the temporary protection of the other amino acid side chains of the molecule groups are used which may be subsequently eliminated by the effect of hydrogen-fluoride; e.g. in the case of arginine and histidine the p-toluene-sulfonyl group, in the case of serine and tyrosine the benzyl group.

If desired, the obtained nona- and, resp., decapeptide amide is reacted with a pharmaceutically acceptable acid to form an acid addition salt or, if desired, the free base is deliberated from the acid addition salt by reacting it with a base and, if desired, the obtained nona- and, resp., decapeptide amide is transformed to a metal complex.

According to the invention pharmaceutical compositions can be prepared by admixing a compound of general formula (I) or a pharmaceutically acceptable salt or complex thereof with carrier and/or supporting agents in tablet, dragée, capsule, suppository, injectable solution, nose-spray etc. form.

An advantageous representative of the compounds of general formula (I) is the compound of formula (XI)

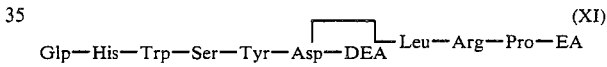

which produced at androgenized test rats an ovulation of higher efficacy than the native LH-RH, despite the fact that the compound of formula (XI) exerted an order of magnitude lower LH-releasing effect than the native LH-RH.

In an other test, on the effect of 20 μg/kg of the compound of formula (XI) sterlet and catfish mother fishes put down their roe to 80% while at the control group to which under the same conditions the D-Phe[6], desGly[10]-LH-RH-ethylamide, known as superactive in literature, was administered no ovulation occurred.

A 100 μg/dose of the compound of formula (XI) administered i.m. simultaneously with the insemination increased the pregnancy ratio of cattle by 25 to 30% while the same dose of the native LH-RH was not efficacious.

With a single dose of 10 μg of the compound of formula (XI) extra-seasonal rutting of blue and silver foxes could be caused, while the native LH-RH proved to be inefficacious at this time.

Another compound according to the invention, the (β-Asp-alpha-anilide)[6]-LH-RH increased the sperm and testosterone production of turkey-cocks much better and longer than e.g. the D-Phe[6]-LH-RH having an analogous structure. The same compound essentially reduced the brooding time of female turkeys while the native LH-RH was ineffective.

The above examples prove that the novel gonadoliberine analogues according to the invention exert a strong effect on the reproductive processes of vertebrates.

Their advantageous application is proved by numerous tests in the animal husbandry.

An essential advantage of the compounds of general formula (I) in contradiction to the known gonadoliberine analogues of high effect is that they are built exclusively of L-amino acids, at the same time their ovulation-inducing and testerone-releasing effects examined in biological tests were better than those of the so-called superactive gonadoliberine derivatives containing glycine or D-amino-acid in position 6.

For the compounds according to the invention and their preparation the following examples are given. In the examples the thin-layer chromatographic $R_f$-values on Kieselgel DC, Alufolien/Merck plates were determined in the following solvent mixtures:

| | | |
|---|---|---|
| 1. ethyl acetate - pyridine - acetic acid - water | 60:20:6:11 |
| 2. ethyl acetate - pyridine - acetic acid - water | 120:20:6:11 |
| 3. ethyl acetate - pyridine - acetic acid - water | 240:20:6:11 |
| 4. ethyl acetate - pyridine - acetic acid - water | 480:20:6:11 |
| 5. ethyl acetate - pyridine - acetic acid - water | 30:20:6:11 |
| 6. acetone - chloroform | 1:15 |
| 7. acetone - toluene | 1:1 |
| 8. acetic acid - benzene | 1:7 |
| 9. n-butanol - acetic acid - ethyl acetate - water | 1:1:1:1 |
| 10. n-butanol - acetic acid - water | 4:1:1 |
| 11. n-butanol - acetic acid - water | 4:1:5 (upper phase) |
| 12. ethyl acetate - pyridine - acetic acid - water | 5:5:1:3 |
| 13. butanol - pyridine - acetic acid - water | 60:20:6:11 |

The melting points are given in °C., the values are not corrected.

EXAMPLE 1

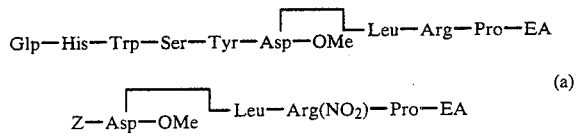

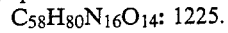
(a)

The hydrobromide salt of 537 mg (1 mmole) of H-Leu-Arg(NO₂)-Pro-EA is dissolved in 10 ml of dimethyl formamide, then at a temperature of 0° C. 447 mg (1 mmole) of a Z-Asp(OPFP)-OMe derivative are added. The pH-value of the reaction mixture is adjusted to 8 by triethyl amine under stirring, then after 6 hours the solution is evaporated in vacuo. The residue is triturated at first with ether and then with water, filtered, finally precipitated from methanol by adding other. Thus 440 mg (62%) of a white, amorphous substance are obtained.

$C_{32}H_{49}N_9O_{10}$: 719.6.
M.p.: 182°-184° C.
$[\alpha]_D^{22} = -58.4°$ (c=1, methanol).
Rf (2)=0.5; Rf (9)=0.85; Rf (12)=0.9.

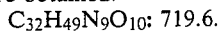
(b)
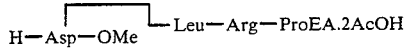

400 mg (0.56 mmole) of the tetrapeptide

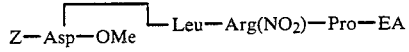

are dissolved in 20 ml of 50 percent acetic acid and hydrogenated in the presence of 50 mg of a 10 percent palladium on charcoal catalyst for 4 hours. The catalyst is filtered off, the acetic acid is eliminated in vacuo and the residue is triturated with ether, filtered and dried in vacuo. Yield: 360 mg (97%).

$C_{28}H_{52}N_8O_{10}$: 660.5.
Rf (1)=0.15; Rf (9)=0.6; Rf (10)=0.25; Rf (5)=0.45.

(c)

716 mg (1 mmole) of the pentapeptide-hydrazide Glp-His-Trp-Ser-Tyr-N₂H₃ are dissolved in 20 ml of dimethyl formamide. The solution is cooled to −10° C. whereafter 0.7 ml of 6N hydrochloric acid solution and then a concentrated aqueous solution of 75 mg of sodium nitrite are added. After stirring for 10 minutes at −5° C. 660 mg (1 mmole) of

diacetate and a cooled solution of 0.7 ml of triethyl amine in 5 ml of dimethyl formamide are added to the reaction mixture. If necessary, the pH-value of the solution is adjusted to 8 with triethyl amine. The solution is stirred for 1 hour at −5° C., then for 12 hours at 0° C. and the dimethyl formamide is eliminated in vacuo. The residue is triturated with ether, filtered, then fractionated in 0.2N acetic acid on a Sephadex G-25 column. The fractions containing the main product are submitted to chromatography on a column of reversed-phase media C₁₈-bonded silica gel (Whatman, LRP-1) in 30 percent aqueous methanol, then the pure fractions are lyophilized. Yield: 712 mg (58%).

$C_{58}H_{80}N_{16}O_{14}$: 1225.
$[\alpha]_D^{22} = -53.4°$ (c=1, water).
Rf (5)=0.5; Rf (10)=0.15; Rf (9)=0.7.
Amino acid analysis: Glu: 1.02; His: 0.97; Ser: 0.95; Tyr: 1.01; Asp: 1.07; Leu: 1.00; Pro: 0.93; Arg: 1.02.

EXAMPLE 2

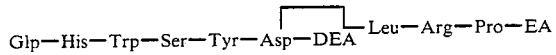

(a) Boc-Asp (OBzl)-DEA 3.23 g (10 mmoles) of tert.-butyloxy-carbonyl aspartic acid-β-benzylester are dissolved in 100 ml of dimethyl formamide at a temperature of 0° C. 1.35 g (10 mmoles) N-hydroxybenztriazole and 2.26 g (11 mmoles) of dicyclohexyl-carbodiimide are added to the solution, then it is stirred for 15 minutes at 0° C., whereafter the solution of 1.0 ml (0.73 g; 10 mmoles) of diethyl amine in 20 ml of ethyl acetate is dropped to the stirred reaction mixture. Stirring is continued for 30 minutes at 0° C., then for 4 hours at room temperature. The precipitate is filtered, the mother liquor is taken up after evaporation in ethyl acetate and repeatedly shaken with a 10 percent cold citric acid solution, saturated sodium-hydrogen-carbonate solution and a saturated sodium-chloride solution. The ethyl-acetate phase is dried over anhydrous sodium sulfate and evaporated in vacuo. 3.6 g (95%) of a pale yellow oil are obtained.

$C_{20}H_{30}N_2O_5$: 378.2.
$[\alpha]_D^{22} = -58.4°$ (c=1, methanol).

Rf (4)=0.95; Rf (6)=0.95; Rf (7)=0.75.

(b) BOC-Asp-DEA 3.8 g (10 mmoles) of tert.-butyloxy-carbonyl-aspartyl-beta-benzylester-alpha-diethyl-amide are dissolved in 50 ml of methanol and hydrogenated in the presence of 300 mg of a 10 percent palladium on charcoal catalyst for 2 hours. After filtering out the catalyst the solution is evaporated and dried in an exsiccator. Thus 2.8 g (100%) of a pale yellow foamy substance are obtained.

$C_{13}H_{25}N_2O_5$: 289.1.
$[\alpha]_D^{22} = -60.1°$ (c=1, methanol).
Rf (4)=0.7; Rf (6)=0.9; Rf (8)=0.8.

(c) BOC-Asp (OPFP)-DEA 2.9 g (10 mmoles) of tert.-butyloxy-carbonyl-aspartic-acid-alpha-diethyl-amide are dissolved in 100 ml of ethyl acetate at 0° C. under stirring, then 1.84 g (10 mmoles) of pentafluoro-phenol and 2.26 g (11 mmoles) of dicyclohexyl-carbodiimide are added. The reaction mixture is stirred at a temperature of 0° C. for 30 minutes, then at room temperature for 24 hours. After filtering out the separated precipitate the ethyl-acetate solution is evaporated, the residue is taken up in petroleum ether (further on: petrolether), the separated precipitate is again filtered off and the solution is evaporated. After drying 4.4 g (99%) of a colourless oil are obtained.

$C_{19}H_{24}N_2O_5F_5$: 455.1.
$[\alpha]_D^{22} = -75.0°$ (c=1, methanol).
Rf (8)=0.95; Rf (6)=0.9; Rf (4)=0.75; Rf (7)=0.8.

(d)

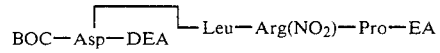

The hydrobromide salt of 536 mg (1 mmole) of H-Leu-Arg(NO₂)-Pro-ethyl-amide is dissolved in 5 ml of dimethyl formamide. The solution is cooled to 0° C., 0.14 ml (1 mmole) of triethyl amine are added, then 453 mg (1 mmole) of tert.-butyloxy-carbonyl-aspartyl-alpha-diethyl-amide-β-pentafluoro-phenylester are added. The reaction mixture is stirred at room temperature for 5 hours while the pH-value is adjusted from time to time to neutral with triethyl amine. After the evaporation of the reaction mixture the remaining substance is triturated with ether and then filtered. The thus-obtained crude product of about 780 mg is purified by chromatography on a silicagel column in a 4:1:1 mixture of n-butanol, acetic acid and water. The appropriate fractions are collected, evaporated to dryness in vacuo and the residue is triturated with ether. Thus 470 mg (64%) of a white powder are obtained.

$C_{32}H_{57}N_{10}O_9$: 725.6.
$[\alpha]_D^{22} = -77.2°$ (c=1, methanol).
M.p.=132°–133° C.
Rf (2)=0.4; Rf (9)=0.85; Rf (10)=0.55.

(e)

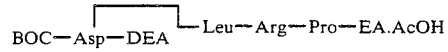

730 mg (1 mmole) of the tetrapeptide

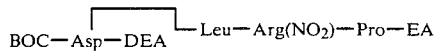

are dissolved in 20 ml of 50 percent acetic acid and hydrogenated in the presence of 100 mg of a 10 percent palladium on charcoal catalyst for 3 hours. After the evaporation of the reaction mixture a chromatographically uniform oily product is obtained.

$C_{34}H_{63}N_9O_9$: 741.6.
Rf (2)=0.05; Rf (9)=0.65; Rf (1)=0.6.

(f)

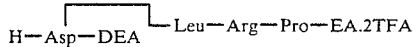

740 mg (1 mmole) of the tetrapeptide

are dissolved in 10 ml of trifluoro-acetic acid and stirred at room temperature for 15 minutes. The solution is evaporated in vacuo. The residue is triturated with ether, filtered and dried over NaOH. Thus 780 mg (96%) of a slightly hygroscopic substance are obtained.

$C_{31}H_{53}O_9N_9F_6$: 809.2.
$[\alpha]_D^{22} = -40.6°$ (c=1, water).
Rf (11)=0.2; Rf (5)=0.4.

(g)

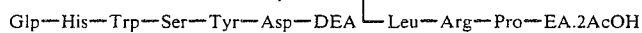

286 mg (0.4 mmole) of the pentapeptide hydrazide Glp-His-Trp-Ser-Tyr-N₂H₃ are dissolved in 25 ml of dimethyl formamide. The solution is cooled to −10° C. and under stirring 0.27 ml of 6N hydrochloric acid, then the concentrated aqueous solution of 30.2 mg of sodium nitrite are dropped to it. After 5 minutes the solution of the trifluoro-acetate salt of 353 mg (0.4 mmole) of the tetrapeptide

prepared in 1 ml of dimethyl formamide with 0.27 ml of triethyl amine of −10° C. is added. If necessary, the reaction mixture is adjusted to a neutral pH-value by triethyl amine, then it is stirred for 1 hour at a temperature of −5° C., for 1 hour at 0° C. and for 12 hours at room temperature.

The dimethyl formamide is eliminated in vacuo, the residue is submitted to chromatography on a silica gel column with a 30:20:6:11 mixture of ethyl acetate, pyridine, acetic acid and water. The appropriate fractions are collected, evaporated in vacuo, triturated with ether, filtered and dried. Thus 290 mg (50%) of a white powder are obtained.

$C_{65}H_{95}N_{17}O_{17}$: 1385.
M.p.: 180°–181° C.
$[\alpha]_D^{22} = -64.2°$ (c=1, methanol).
Rf (12)=0.85; Rf (5)=0.35; Rf (11)=0.25.
Amino acid analysis: Asp: 1.0; Ser: 0.99; Glu: 1.01; Leu: 1.10; Tyr: 1.00; His: 0.92; Arg: 0.98.

EXAMPLE 3

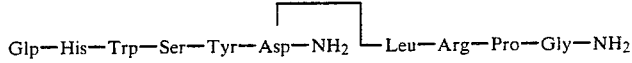

(a) BOC-Asp(OBzl)-OPFP 3.23 g (10 mmoles) of tert.-butyloxy-carbonyl-aspartic acid-β benzyl-ester are dissolved in 50 ml of ethyl acetate. The solution is cooled to 0° C., and under stirring 1.84 g (10 mmoles) of pentafluoro-phenol and 2.26 g (11 mmoles) of dicyclo-hexyl-carbodiimide are added. The reaction mixture is stirred at 0° C. for 30 minutes and at room temperature for 12 hours. After filtering the solution is evaporated in vacuo, the residue is dissolved in 15 ml of ether and, by adding 15 ml of petrolether, crystallized at a temperature of −20° C.

Yield: 3.75 g (70%).
$C_{22}H_{20}N_1O_6F_5$: 489.3.
M.p.: 84° C.
$[\alpha]_D^{22} = -18.1°$ (c=1, ethyl acetate).
Rf (7)=0.9; Rf (4)=0.95.

(b) BOC-Asp(OBzl)-NH$_2$

To the solution of 970 mg (2 mmoles) of tert.-butyloxy-carbonyl-aspartic acid-β-benzylester-alpha-pentafluoro-phenylester in 10 ml of methanol 10 ml of methanol saturated with ammonia at 0° C. are added and stirred at 0° C. for 30 minutes. The solvent is evaporated in vacuo, the residue is crystallized from the mixture of methanol and ether.

Analysis for the formula $C_{16}H_{22}N_2O_5$ (322.1): calculated: C 59.62; H 6.83; N 8.69; found: C 59.2; H 6.98; N 8.8.

M.p.: 159°–161° C.
$[\alpha]_D^{22} = +1.1°$ (c=1, methanol).
Rf (7)=0.5; Rf (8)=0.75; Rf (4)=0.9; Rf (6)=0.95.

(c) BOC-Asp-NH$_2$ 480 mg (1.5 mmoles) of tert.-butyloxy-carbonyl-aspartic acid-β-benzylester-alpha-amide are dissolved in 10 ml of methanol and hydrogenated in the presence of 50 mg of a 10 percent palladium in charcoal catalyst for 1 hour. After filtering off the catalyst the solvent is evaporated in vacuo and the residue is crystallized from aqueous ethanol.

Yield: 246 mg (93%).
$C_9H_{16}N_2O_5$: 232.2.
M.p.: 145°–146° C.
$[\alpha]_D^{22} = -2.2°$ (c=1, methanol).
Rf (7)=0.05; Rf (8)=0.2; Rf (4)=0.3; Rf (6)=0.1.

according to Example 3/c is used. 72 mg (12%) of a pure substance are obtained.

$C_{57}H_{79}N_{18}O_{14}$=1239.
$[\alpha]_D^{22} = -55.5°$ (c=1, water).
Rf (5)=0.35; Rf (11)=0.15; Rf (9)=0.65; Rf (13)=0.15.

Amino acid analysis: Glu: 0.96; His: 1.04; Ser: 0.93; Tyr: 1.02; Leu: 1.02; Pro: 0.94; Gly: 1.00; Asp: 1.1.

EXAMPLE 4

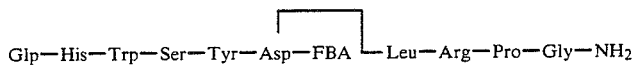

(a) BOC-Asp(OBzl)-α-[2-(4-chlorophenyl)-isobutyl-amide]

5 g (15 mmoles) of tert.-butyloxy-carbonyl-aspartic acid-β-benzylester are dissolved in 100 ml of ethyl-acetate, cooled to 0° C., and 2.1 g N-hydroxy-benztriazole, 3.75 g of dicyclohexyl-carbodiimide and the solution of 3.5 g of 2-(4-chlorophenyl)-isobutyl-amine in 20 ml of dimethyl-formamide are added to the stirred reaction mixture. The mixture is stirred at room temperature for 12 hours, then the solution is filtered. The ethyl-acetate solution is shaken out with 10 percent citric acid solution, saturated sodium-hydrogen-carbonate solution and saturated sodium-chloride solution, dried over anhydrous sodium sulfate, filtered and evaporated in vacuo. The remaining colourless oil slowly crystallizes. The crystals are washed with a mixture of ether and petrol ether, then dried.

Yield: 5.5 g (75%).
$C_{26}H_{33}N_2O_5Cl$: 488.2.
M.p.: 60°–61° C.
$[\alpha]_D^{22} = -12.2°$ (c=1, methanol).
Rf (7)=0.75; Rf (8)=0.6.

(b) BOC-Asp-FBA

The solution of 2.3 g (4.7 mmoles) of tert.-butyloxy-carbonyl-aspartic acid-δ-benzylester-alpha-[2-(p-chlorophenyl)-isobutyl-amide] in 30 ml of methanol is hydrogenated in the presence of 200 mg of a 10 percent palladium on charcoal catalyst for 2 hours, then the catalyst is filtered off and the solvent is evaporated in vacuo. The residue is triturated in ether and crystallized from methanol with ether.

Yield: 1.5 g (87%).
Analysis for the formula $C_{19}H_{28}N_2O_5$ (364.2): calculated: C 62.63; H 7.69; found: C 62.3; H 7.58.

(d)

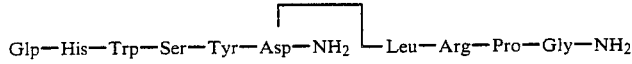

The synthesis of the peptide in solid phase, the cleaving from the polymer with hydrogen-fluoride as well as the chromatographic purification of the crude peptide are carried out as described in Example 4/c with the difference that as 6-amino acid the compound prepared M.p.: 94°–96° C.
$[\alpha]_D^{22} = -19°$ (c=1, methanol).
Rf (3)=0.2; Rf (2)=0.3; Rf (7)=0.15; Rf (8)=0.8; Rf (10)=0.15.

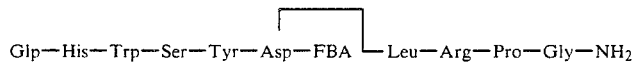
(c)

1 g (0.5 mmole) of benzhydryl-amine polymer is put into the reaction vessel of an automatic peptide synthetizator (Beckman 99OB) and stirred in 30 ml of dichloromethane for 4 hours. The protected amino acid derivatives are coupled with the polymer in an appropriate sequence by a cyclic repetition of the following (1–10.) steps:

1. washing with 30 ml of dichloromethane—3×3 minutes
2. washing with 30 ml of a 1:2 mixture of trifluoro acetic acid and dichloro-methane—5 and 25 minutes
3. washing with 30 ml of dichloro-methane—3×3 minutes
4. washing with 30 ml of ethanol—3×3 minutes
5. washing with 30 ml of chloroform—3×3 minutes
6. washing with 30 ml of a 1:9 mixture of triethyl amine and chloroform—2×10 minutes
7. washing with 30 ml of chloroform—3×3 minutes
8. washing with 30 ml of dichloromethane—3×3 minutes
9. incubation of 1.5 mmoles of BOC-amino acid derivative and 1.5 mmoles of diisopropyl-carbodiimide in 30 ml of dichloro-methane—120 minutes
10. washing with 30 ml of dichloro-methane—3×3 minutes.

The protected amino acid derivatives are as follows: BOC-Gly-OH, BOC-Pro-OH, BOC-Arg(Tos)-OH, BOC-Leu-OH, BOC-Asp-FBA, BOC-Tyr(Bzl)-OH, BOC-Ser(Bzl)-OH, BOC-Trp-OH, BOC-His(Tos)-OH and Glp.

After coupling all amino acids the ready peptide polymer resin is dried in vacuo and stirred with 50 ml of condensed hydrogen-fluoride at 0° C. in the presence of 6 ml of anisole for 45 minutes. The hydrogen fluoride is eliminated in an anhydrous nitrogen gas stream, the residue is precipitated with ether and filtered. The filtered substance is suspended in 50 percent acetic acid, filtered and the filtrate is evaporated in vacuo. The residue is led through a Sephadex G-25 column in 50 percent acetic acid solution. The pure main fraction is submitted to chromatography on a silica gel column with solvent mixture 10. The fractions containing the pure substance are evaporated and lyophilized.

Yield: 70 mg (10%).
$C_{67}H_{91}N_{18}O_{14} = 1371$.
$[\alpha]_D^{22} = -56.4°$ (c=1, water).
Rf (13)=0.25; Rf (9)=0.7; Rf (11)=0.2; Rf (5)=0.5.

Amino acid analysis: Glu: 0.97; His: 1.05; Ser: 0.94; Pro: 0.95; Tyr: 1.02; Asp: 1.02; Leu: 1.01; Gly: 1.00.

EXAMPLE 5

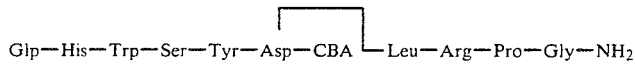

(a) BOC-Asp(OBzl)-CBA 2.4 g (5 mmoles) of the tert.-butyloxy-carbonyl-aspartic acid-β-benzylester-alpha-pentafluoro-phenylester prepared according to Example 3/a are dissolved in 20 ml of ethyl acetate, cooled to 0° C., and the cooled solution of 0.42 ml (5 mmoles) of cyclobutyl-amine in 2 ml of ethyl acetate are dropped to it. The reaction mixture is stirred for 2 hours at room temperature, then washed with 10 percent citric acid solution, saturated sodium-hydrogen-carbonate solution and saturated sodium-chloride solution, dried over anhydrous sodium sulfate, filtered and evaporated in vacuo. The residue is crystallized from ether with petrol ether.

Yield: 1.16 g (89%).
$C_{20}H_{28}N_2O_5$: 376.2.
M.p.: 84°–86° C.
$[\alpha]_D^{22} = -5.7°$ (c=1, methanol).
Rf (8)=0.9; Rf (10)=0.9; Rf (7)=0.75; Rf (11)=0.95.

(b) BOC-Asp-CBA 1 g (2.65 mmoles) of tert.-butyloxy-carbonyl-aspartic acid-β-benzylester-alpha-cyclobutyl-amide is dissolved in 20 ml of methanol and hydrogenated in the presence of 100 mg of a 10 percent palladium in charcoal catalyst for 2 hours. After filtering off the catalyst the solution is evaporated in vacuo and the residue is crystallized from aqueous ethanol.

Yield: 600 mg (79%).
Analysis for the formula $C_{13}H_{22}N_2O_5$ (286.1): calculated: C 54.54; H 7.69; found: C 53.9; H 7.68.
M.p.: 149°–150° C.
$[\alpha]_D^{22} = -9.5°$ (c=1, methanol).
Rf (8) 0.2; Rf (10)=0.75; Rf (7)=0.05.

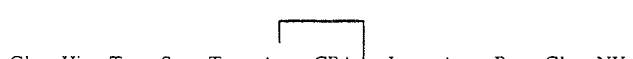
(c)

The solid-phase synthesis of the peptide, the splitting off from the polymer with hydrogen-fluoride as well as the chromatographic purification of the crude peptide are carried out as described in Example 4/c with the difference that as 6-amino acid the compound prepared according to Example 5/b is used. Thus 68 mg (10.5%) of the pure peptide are obtained.

$C_{61}H_{85}N_{18}O_{14}$: 1291.
$[\alpha]_D^{22} = -44.8°$ (c=1, water).
Rf (11)=0.2; Rf (9)=0.7; Rf (13)=0.2; Rf (5)=0.4
Amino acid analysis: Glu: 1.05; His: 0.96; Ser: 0.94; Tyr: 0.98; Asp: 1.07; Leu: 1.02; Pro: 0.96; Gly: 1.00.

EXAMPLE 6

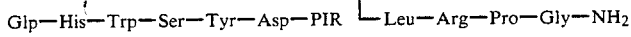

(a) BOC-Asp(OBzl)-PIR 3.2 g (10 mmoles) of tert.-butyloxy-carbonyl-aspartic acid-β-benzylester are dissolved in 5 ml of ethyl acetate, and at a temperature of 0° C. 1.35 g of N-hydroxy-benztriazole, 2.26 g of dicyclohexyl-carbodiimide and the solution of 0.8 ml of pyrrolidine in 2 ml of ethyl acetate are added. The reaction mixture is stirred for 2 hours at room temperature, then shaken out with 10 percent citric acid solution, saturated sodium-hydrogen-carbonate solution and saturated sodium-chloride solution. The organic phase is dried over anhydrous sodium-sulfate, filtered and evaporated in vacuo. The residue is dissolved in ether, filtered and again evaporated. Thus 3.4 g (90%) if an oil are obtained.

$C_{20}H_{28}N_2O_5$: 376.2.
$[\alpha]_D^{22} = -84.4°$ (c=1, methanol).
Rf (7)=0.75; Rf (4)=0.95; Rf (8)=0.85; Rf (6)=0.8.

(b) BOC-Asp-PIR

The solution of 3 g (8 mmoles) of tert.-butyloxycarbonyl-aspartic acid-β-benzylester-alpha-pyrrolidine in 30 ml of methanol is hydrogenated in the presence of 250 mg of a 10 percent palladium on charcoal catalyst for 2 hours, then the catalyst is filtered off and the solution is evaporated. The remaining oil is dried over sulfuric acid.

Yield: 21.1 g (92%).
$C_{13}H_{22}N_2O_5$: 286.2.
M.p.: 124°-125° C.
$[\alpha]_D^{22} = -39.9°$ (c=1, methanol).
Rf (8)=0.3; Rf (7)=0.2.

tion, dried over anhydrous sodium sulfate and evaporated. The remaining oil is crystallized from ethanol with water.

Yield: 3.7 g (89%).
$C_{24}H_{28}N_2O_5$: 424.1.
M.p.: 75°-76° C.
$[\alpha]_D^{22} = -70.9°$ (c=1, ethanol).
Rf (7)=0.9.

(b) H-Asp(OBzl)-IND.TFA 800 mg (1.9 mmoles) of tert.-butyloxy-carbonyl-aspartic acid-β-benzylester-alpha-indoline are dissolved in 5 ml of trifluoro-acetic acid and stirred at room temperature for 15 minutes. The trifluoro-acetic acid is eliminated in vacuo and the residue is triturated with ether, filtered, dried, then crystallized from ethanol with ether.

Yield: 780 mg (94%).
$C_{21}H_{21}N_2O_5F_3$: 438.1.
M.p.: 114°-115° C.
$[\alpha]_D^> = -5.8°$ (c=1, methanol).
Rf (7)=0.2; Rf (4)=0.65.

(c) Glp-His-Trp-Ser-Tyr-Asp(OBzl)-IND 716 mg (1 mmole) of the pentapeptide-hydrazide Glp-His-Trp-Ser-Tyr-$N_2H_3$ are dissolved in 10 ml of dimethyl formamide. The solution is cooled to −10° C., then the concentrated aqueous solution of 0.7 ml of 6N hydrochloric acid and 75 mg of sodium nitrite is added. The reaction mixture is stirred at −5° C. for 10 minutes, then the solution of the trifluoroacetate salt of 438 mg (1 mmole) of H-Asp(OBzl)-indoline prepared with 0.7 ml

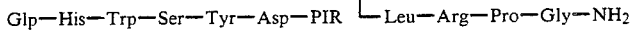

(c)

The solid-phase synthesis of the peptide, the splitting off from the polymer with hydrogen fluoride as well as the chromatographic purification of the crude peptide are carried out according to Example 4/c with the difference that as 6-amino acid the compound prepared according to Example 6/b is used. Thus 78 mg (12%) of the pure peptide are obtained.

$C_{61}H_{85}N_{18}O_{14}$: 1293.
$[\alpha]_D^{22} = -53.2$ (c=1, water).
Rf (13)=0.15; Rf (9)=0.6; Rf (11)=0.2; Rf (5)=0.4.
Amino acid analysis: Gly: 0.97; His: 1.01; Ser: 0.94; Tyr: 1.03; Asp: 1.05; Leu: 1.00; Pos: 0.94.

EXAMPLE 7

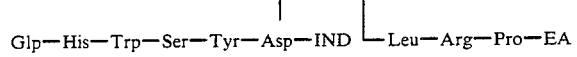

(a) BOC-Asp(OBzl)-IND 3.23 g (10 mmoles) of tert.-butyloxy-carbonyl-aspartic acid-β-benzylester are dissolved in 50 ml of ethyl acetate. The solution is cooled to 0° C. and under stirring 2.3 g of dicyclohexyl-carbodiimide and 1.19 g of indoline are added. The reaction mixture is allowed to be stirred overnight at room temperature, then it is filtered the next day, the filtrate is washed 3 times each with 10 percent citric acid, saturated sodium-hydrogencarbonate solution and saturated sodium-chloride soluof triethyl amine and 2 ml of dimethyl formamide is added. If necessary, the pH-value is adjusted to 8 with triethyl amine. The mixture is stirred at −5° C. for 1 hour and at 0° C. for 12 hours. The dimethyl formamide is distilled off in vacuo, the residue is triturated with water, filtered, washed with ethanol and ethyl acetate, then dissolved in dimethyl formamide, treated with charcoal while hot and crystallized by adding ether.

Yield: 600 mg (60%).
$C_{53}H_{56}N_{10}O_{11}$: 1008.9.
M.p.: 172°-174° C.
Rf (9)=0.7; Rf (10)=0.4; Rf (1)=0.35.

(d) Glp-His-Trp-Ser-Tyr-Asp-IND

The solution of 500 mg (0.5 mmoles) of the hexapeptide Glp-His-Trp-Ser-Tyr-Asp(OBzl)-IND in 0.5 ml of dimethyl formamide and 30 ml of 50 percent acetic acid solution is hydrogenated in the presence of 50 mg of a 10 percent palladium on charcoal catalyst for 2 hours. After filtering off the catalyst the solvent is evaporated in vacuo and the residue is crystallized from dimethyl formamide with ether.

Yield: 380 mg (83%).
M.p.: 219°-221° C.
$[\alpha]_D^{22} = -37.7°$ (c=1, dimethyl formamide).
Rf (9)=0.6; Rf (10)=0.4; Rf (1)=0.1.

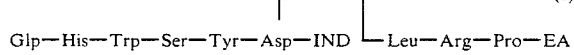 (e)

The solution of 42 mg (0.044 mmoles) of the hexapeptide Glp-His-Trp-Ser-Tyr-Asp-IND in 1 ml of dimethyl formamide is cooled to 0° C. and 7.8 μl of diisopropyl carbodiimide are added. After stirring for 10 minutes the solution in dimethyl formamide of 20 mg (0.044 mmoles) of H-Leu-Arg-Pro-EA hydrochloride neutralized with triethyl amine is added. The reaction mixture is stirred at room temperature for 12 hours, then the solvent is evaporated in vacuo. The residue is submitted the chromatography on a Sephadex G-25 column in 0.2N acetic acid. The fractions containing the main product are collected and lyophilized.

Yield: 28 mg (48%).

$C_{65}H_{85}N_{17}O_{13}$: 1311.

$[\alpha]_D^{22} = 39.6°$ (c=0.25; 25% acetic acid.

Rf (13)=0.8; Rf (9)=0.75; Rf (5)=0.7; Rf (10)=0.5.

EXAMPLE 8

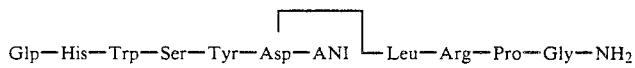

(a) BOC-Asp(OBzl)-ANI 3.23 g (10 mmoles) of tert.-butyloxy-carbonyl-aspartic acid-beta-benzylester are dissolved in 50 ml of ethyl acetate, cooled to 0° C. and 0.96 g of aniline and 2.26 g of dicyclohexyl-carbodiimide are added. The reaction mixture is stirred at room temperature for 6 hours, the solution is filtered off, then washed with 10 percent citric acid solution, saturated sodium-hydrogen-carbonate solution and saturated sodium-chloride solution, dried over anhydrous sodium-sulfate and evaporated in vacuo. The crystals obtained after the evaporation are triturated with petrolether, filtered and dried.

Yield: 4 g (96%).

$C_{22}H_{26}N_2O_5$: 398.3.

M.p.: 105°–106° C.

$[\alpha]_D^{22} = -6°$ (c=1; dimethyl formamide).

Rf (11)=0.8; Rf (12)=0.95; Rf (8)=0.4

(b) BOC-Asp-ANI 3 g of tert.-butyloxy-carbonyl-aspartic acid-beta-benzylester-alpha-anilide are dissolved in 20 ml of methanol and hydrogenated in the presence of 300 mg of a 10 percent palladium on charcoal catalyst. The catalyst is filtered off, the solvent is evaporated in vacuo and the residue is crystallized from ethanol with water.

Yield: 2.05 g (88%).

Analysis for the formula $C_{15}H_{20}N_2O_5$ (308.2): calculated: C 58.44; H 6.49; found: C 58.6; H 6.56.

M.p.: 157°–158° C.

$[\alpha]_D^{22} = -12°$ (c=1, dimethyl formamide).

Rf (11)=0.7; Rf (12)=0.85; Rf (8)=0.05.

The solid-phase synthesis of the peptide, the splitting off from the polymer with hydrogen fluoride as well as the chromatographic purification of the crude peptide are carried out according to Example 4/c with the difference that as 6-amino acid the compound prepared according to Example 8/b is used. Thus 82 mg (12.5%) of the pure product are obtained.

$C_{63}H_{83}N_{18}O_{14}$: 1315.

$[\alpha]_D^{22} = -58.3°$ (c=1, water).

Rf (9)=0.5; Rf (10)=0.2; Rf (12)=0.8.

Amino acid analysis: NH₃: 1.23; Arg: 095; Asp: 1.1; Glu: 1.08; Pro: 1.01; Gly: 1.00; Leu: 1.1; Tyr: 0.85; Ser: 0.99.

What we claim is:

1. Gonadoliberine derivatives of the formula (I)

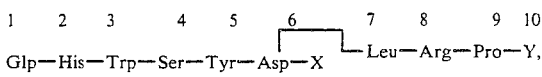

wherein

X represents an —O—R group, wherein R is a benzyl group or a $C_{1-4}$ alkyl group, and

group, wherein R1 and R2 independently stand for hydrogen, a $C_{1-5}$ alkyl, aryl, or aryl-$C_{1-2}$-alkyl group, or they stand together with the adjacent nitrogen atom for a morpholino, 1-indolinyl or 1-pyrrolidinyl group, Y is a glycine amide or a $C_{1-4}$-alkylamide group, and therapeutically acceptable salts thereof.

2. A compound selected from the group consisting of

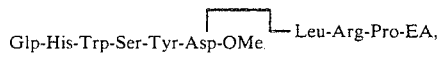

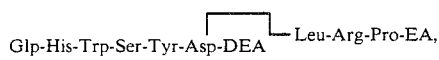

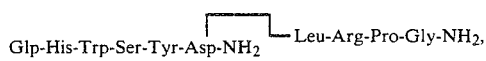

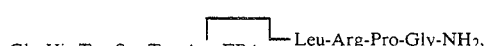

(c)

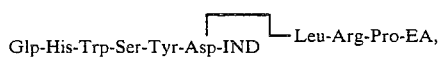

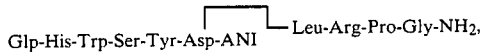

and the therapeutically acceptable salts thereof.

3. A pharmaceutical composition which increases the LH-releasing and the FSH-releasing effect on the reproductive process of vertebrates, comprising an effective amount of a compound of the formula (I) according to claim 1, or a pharmaceutically acceptable salt thereof, in admixture with a pharmaceutically acceptable carrier.

* * * * *